(12) United States Patent
Benvegnu' et al.

(10) Patent No.: US 8,807,996 B2
(45) Date of Patent: Aug. 19, 2014

(54) DEVICE FOR FIXING ORTHODONTIC DEVICES

(75) Inventors: Marco Benvegnu', Thiene (IT); Giuliano Bortolo Maino, Vicenza (IT)

(73) Assignee: HDC SRL, Sarcedo (VI) (IT)

( * ) Notice: Subject to any disclaimer, the term of this patent is extended or adjusted under 35 U.S.C. 154(b) by 0 days.

(21) Appl. No.: 13/130,883

(22) PCT Filed: Dec. 29, 2009

(86) PCT No.: PCT/EP2009/068011
§ 371 (c)(1),
(2), (4) Date: Aug. 25, 2011

(87) PCT Pub. No.: WO2010/076328
PCT Pub. Date: Jul. 8, 2010

(65) Prior Publication Data
US 2011/0300503 A1   Dec. 8, 2011

(30) Foreign Application Priority Data

Dec. 31, 2008   (IT) .............................. V12008A0312

(51) Int. Cl.
*A61C 3/00*   (2006.01)
*A61C 7/00*   (2006.01)
*A61C 8/00*   (2006.01)
(52) U.S. Cl.
CPC *A61C 7/00* (2013.01); *A61C 8/0096* (2013.01)
USPC ........................................... 433/10; 433/174

(58) Field of Classification Search
USPC ........... 433/2, 10, 18, 172, 173, 174, 8, 9, 11, 433/12, 13, 14, 15, 16, 17
See application file for complete search history.

(56) References Cited

U.S. PATENT DOCUMENTS

| 2,011,575 | A | 8/1935 | Ford |
| 2,104,192 | A * | 1/1938 | Ford ................................ 433/10 |
| 5,993,213 | A | 11/1999 | Schiel et al. |
| 2005/0227197 | A1* | 10/2005 | Lin ................................ 433/18 |
| 2006/0069389 | A1 | 3/2006 | Knopfle |

FOREIGN PATENT DOCUMENTS

| WO | WO-2007/128969 A2 * | 11/2007 | .............. A61C 8/00 |
| WO | 2008045908 A2 | 4/2008 | |

* cited by examiner

*Primary Examiner* — Eric Rosen
(74) *Attorney, Agent, or Firm* — Husch Blackwell LLP

(57) ABSTRACT

A fixing device (1; 20) for orthodontic devices which includes a screw (2; 40) complete with an operating head (3; 42) with longitudinal slots (4; 45) for the insertion of orthodontic devices and a threaded shank (5) designed to be screwed inside the patient's oral cavity; apparatus for fixing orthodontic devices contained inside the operating head (3; 42). The fixing apparatus includes a shaped body (6) engaging inside a recess (7, 47) in the operating head (3; 42) and revolvable inside the recess (7; 47). The shaped body (6) has a through opening (8) for the insertion of the orthodontic device and opposing apparatus that anchor the orthodontic device to the operating head (3; 42) when the shaped body (6) is rotated inside the recess (7; 47) after the orthodontic device has been inserted in the through opening (8) and in the longitudinal slots (4; 45).

11 Claims, 9 Drawing Sheets

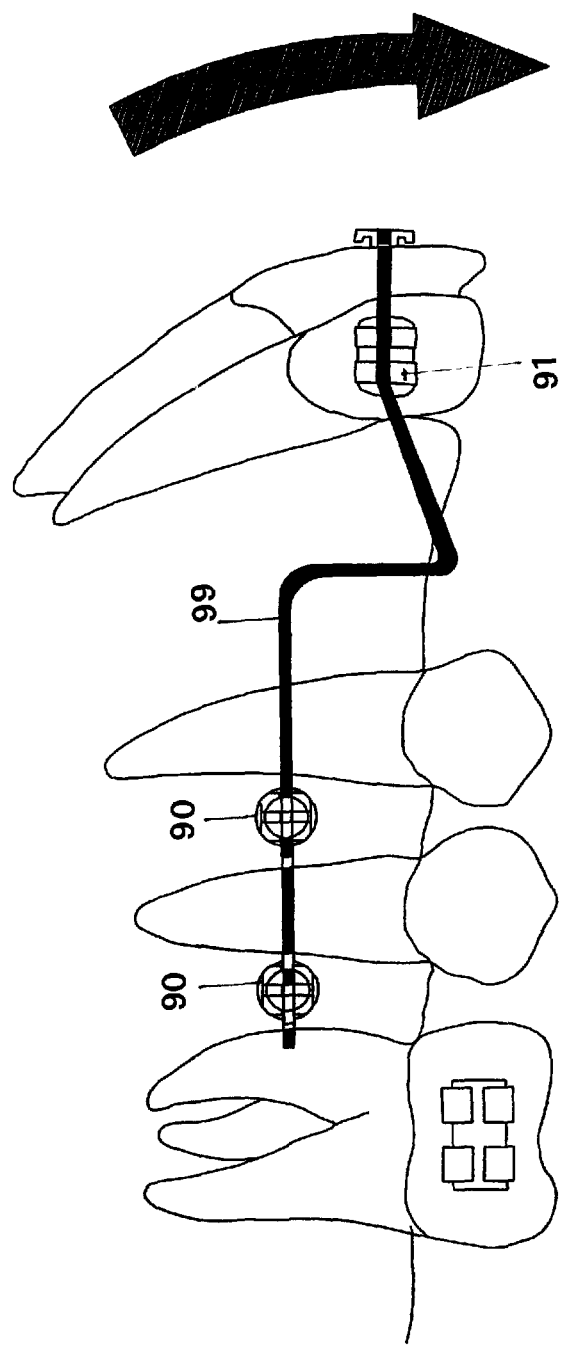

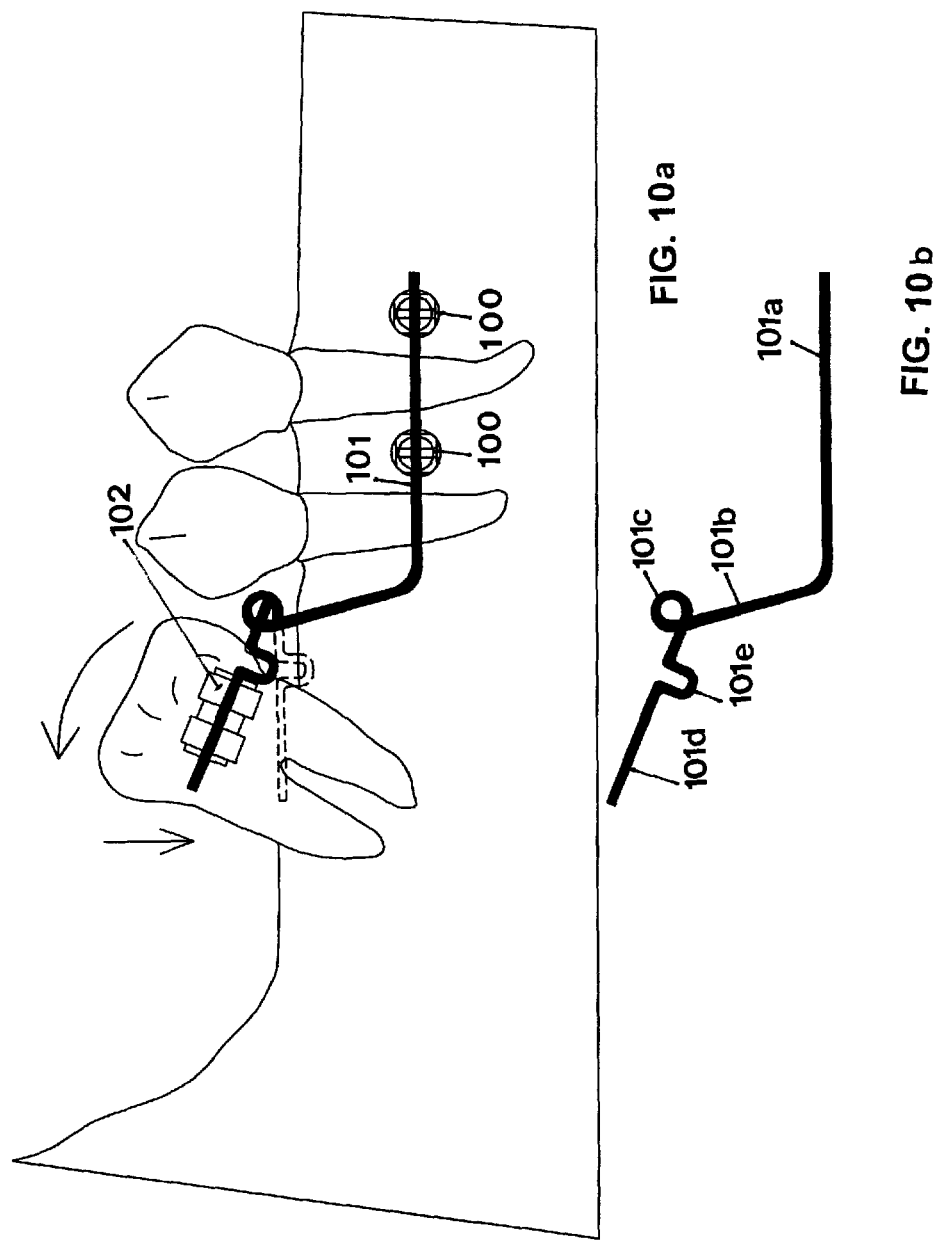

DEVICE FOR FIXING ORTHODONTIC DEVICES

FIELD OF THE INVENTION

The present invention relates to an improved device for fixing orthodontic devices.

It should be noted, first of all, that the term orthodontic devices is used in the present description and in the claims to mean any device or part thereof (wire, plate, grid, etc.) designed to correct dental malformations.

BACKGROUND OF THE INVENTION

According to the known state of the art, dental malformations (or malocclusions) are corrected by means of the use of orthodontic screws, to bands and brackets that enable the application and locking of orthodontic wires.

Brackets are devices that are attached to the surface of the tooth and used to enable the passage of an orthodontic wire that is laid thereon and fixed with metal and/or elastic bindings or a snap-fastening (self-ligating bracket).

The tensioning of the orthodontic wire (and consequently also of the teeth) is done by attaching bindings between the wire and the brackets, or by inserting the wires inside self-ligating brackets, or by using elastic bands and/or springs, or by activating suitably modeled wires.

Orthodontic screws are inserted in the bone through the soft tissues and the part emerging from the gum or oral mucosa is shaped so as to allow for the anchoring of orthodontic treatment devices, such as elastic bands, springs and orthodontic wires.

The orthodontic screws of known type can therefore allow for the passage of the wire but they do not anchor it in position and a manual action by the operator is consequently always needed to bind the orthodontic wire with a metal and/or elastic ligature to the head of the screw, or to wind the wire around the screw in order to fix it in place, or to apply a bonding substance (e.g. a composite and/or acrylic resins) between the wire and the head of the screw.

Such fixing solutions, involving the winding of the wire or the use of a second (metallic or elastic) binding, or ligature, or the application of other substances, are time-consuming and not very practical, especially when action is being taken in regions that are difficult for the operator to access (e.g. the palate or the molar and premolar areas), and they are sometimes not very safe because they carry the risk of the orthodontic wire slipping from the screw.

In this last case, it would be necessary to take action again, causing considerable discomfort to the patient as well.

According to the current state of the art, moreover, relying exclusively on the teeth as a means of anchorage cannot ensure a stable anchorage for the correction of malocclusions so it has to be reinforced with the aid of extraoral means, such as extraoral traction devices, or the use of elastic bands placed between the arches (intra-oral elastic bands) that always require the cooperation of the patient.

Being attached to the bone, the orthodontic screw enables a stable and to predictable anchorage to be achieved and consequently allows for the correction of malocclusions without needing the patient's cooperation.

BRIEF SUMMARY OF THE INVENTION

The object of the present invention is to overcome the previously-discussed drawbacks.

In particular, the main object of the present invention is to produce a device for fixing orthodontic wires that avoids the need to wrap the wire around the shaft of the orthodontic screw and/or to fix the wire with metallic and/or elastic ligatures, and/or to apply other bonding substances, such as acrylic resins and/or composites.

Another object of the present invention is to produce a device for fixing orthodontic devices that is easier to use than the fixing devices used at present.

The above objects are achieved by the present invention relating to a device for fixing orthodontic devices, the main characteristics of which are as described in the content of the first claim.

The fixing device according to the present invention is advantageously removable and allows for the orthodontic device to be detached, retaining the opportunity to anchor it again thereafter, without having to remove the orthodontic screw to which it was anchored as well.

Another advantage of the fixing device according to the present invention lies in that it enables several stable anchoring points to be provided for orthodontic devices for use in correcting dental malformations so that the latter can be kept attached to the device and so as to avoid their removal from the patient's head and/or their sliding, depending on the dimensions and/or cross sections of said orthodontic devices.

Another advantage of the fixing device according to the present invention lies in that it can be implanted in different parts of the oral cavity also to anchor various types of orthodontic devices other than orthodontic wires.

BRIEF DESCRIPTION OF THE DRAWINGS

The above objects and advantages will be better clarified in the description of preferred embodiments, that are given herein as non-limiting examples with reference to the attached drawings, wherein:

FIGS. 9a and 9b show an orthodontic system using fixing devices according to the invention, inserted in the interradicular space;

FIG. 10a shows an orthodontic system using fixing devices according to the invention, inserted in the alveolar bone;

FIG. 10b shows the shape of the orthodontic wire used in the orthodontic system in FIG. 10a.

DETAILED DESCRIPTION OF THE INVENTION

Figure 1:
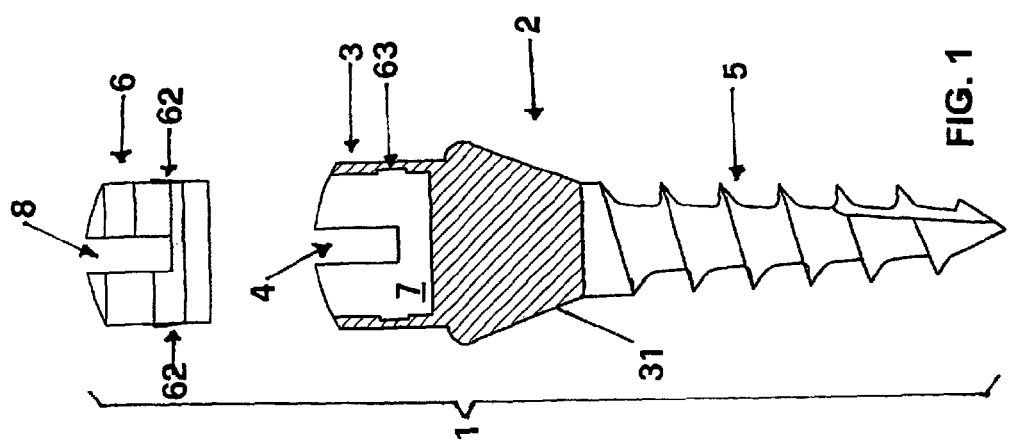
FIG. 1 shows an exploded, partially cross-sectional view of the fixing device according to the invention.

As shown in FIG. 1, the fixing device for anchoring orthodontic wires forming the object of the invention, globally indicated by the numeral 1, comprises a screw 2 complete with an operating head 3 with longitudinal slots 4 for the insertion of orthodontic wires, and a threaded shaft 5 that is screwed into the patient's oral cavity.

In addition to the longitudinal slots 4, the operating head 3 comprises a base 31 with a trapeze-shaped profile for connecting it to the shaft 5 of the screw 2. According to the present invention, the fixing means comprise a shaped body 6 engaging inside a recess 7, contained in the operating head 3 and complete with a through hole 8 for the insertion of an orthodontic wire F.

Figure 3:
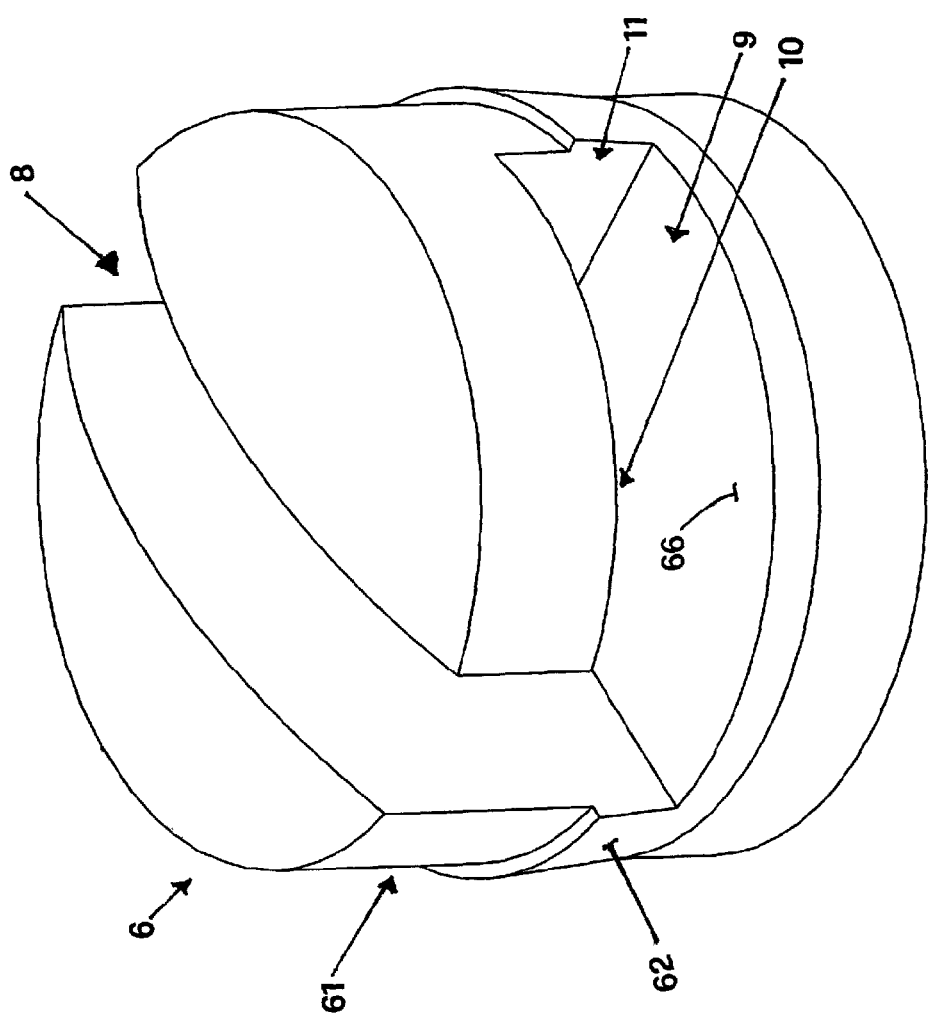
FIG. 3 shows an axonometric view of a detail of FIGS. 1 and 2.

The shaped body 6, shown in detail in FIG. 3, also includes opposing means comprising a shaped slot 9 that is in communication with the through hole 8.

The shaped slot 9 serves the purpose of anchoring the orthodontic wire F to the operating head 3, after the orthodontic wire F has been inserted in the through hole 8 and in the shaped slot 9, when the shaped body 6 is rotated inside the recess 7.

In fact, it is evident that the shaped slot 9 extends on a plane essentially orthogonal to the longitudinal axis X of the screw 2 (FIG. 2) and anchors the orthodontic wire F to the operating head 3 by means of the combined action of the opposing surfaces 10 and 66 that retain the orthodontic wire F (shown in FIG. 4) when the shaped body 6 is rotated inside the recess 7.

The contrasting action of the surface 10 against the orthodontic wire is due to the fact that the opposing surface 10 is tilted in the example in relation to the opposing surface 66, giving the shaped slot 9 a tendency to converge towards the bottom 11.

In another embodiment, not shown in the figures, there may also be two opposing surfaces that tilt and converge towards the bottom of the above-described shaped slot.

With reference to FIG. 3, the shaped body 6 is cylindrical in shape and has an external lateral surface 61.

In order to prevent any slipping of the shaped body 6 from the recess 7 in the operating head 3 after it has been inserted, the shaped body 6 includes, as shown in FIGS. 1 and 3, a ring-shaped projection 62 that is contained inside a corresponding ring-shaped cavity 63 provided on the inside surface of the recess 7 for containing the shaped body 6.

Figure 2:
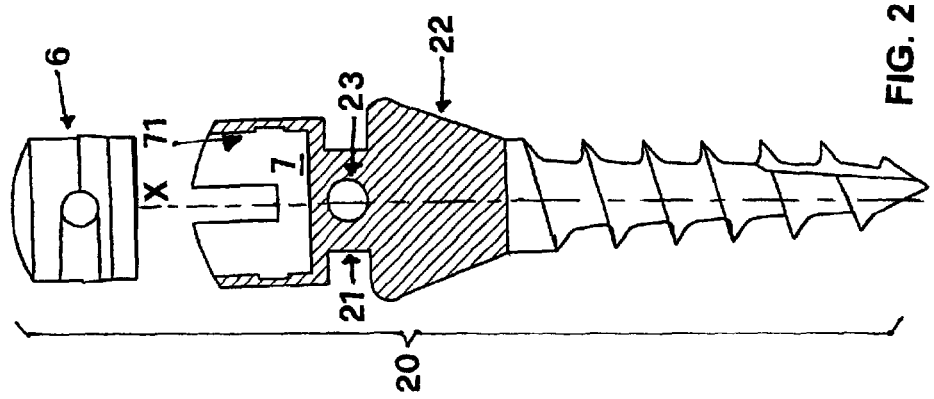
FIG. 2 shows an exploded, partially cross-sectional view of another embodiment of the device in FIG. 1.

FIG. 2 shows another embodiment of the fixing device 1, now indicated by the numeral 20, which differs from that of FIG. 1 in that it includes a narrowed section 21 in the base 22. This narrowed section 21 has a through hole 23 for the insertion and anchorage of additional orthodontic wires.

In other embodiments of the invention, not illustrated herein, there may be more than one through hole in the narrowed section.

Figure 4:
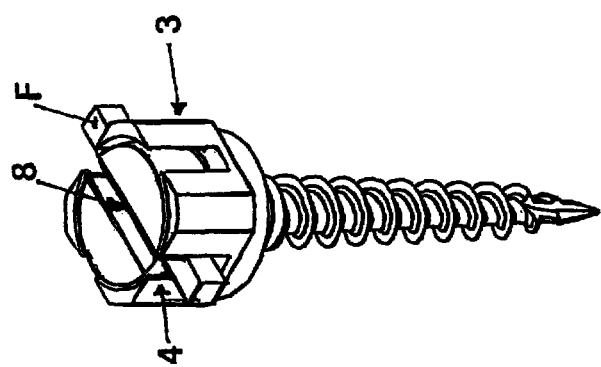

Operatively, the orthodontic wire F is inserted in the through hole 8 when it is placed in communication with the longitudinal slot 4, as shown in FIG. 4.

Once the orthodontic wire F has been inserted, the shaped body is rotated by the operator through 90° with the aid, for instance, of a screwdriver (not shown in the figure) and the orthodontic wire F is anchored inside the shaped slot 9 against the opposing surface 10.

Figure 5:
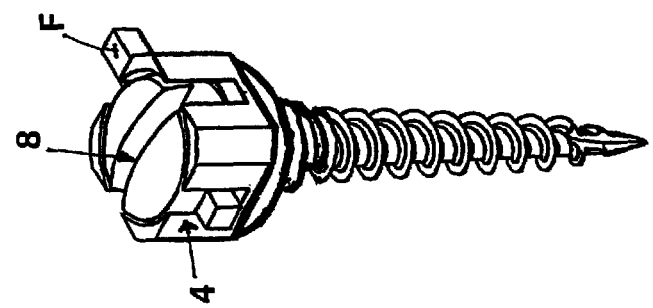
FIGS. 4 and 5 show an axonometric view of two different operative phases for the fixing device according to the invention.

As shown in FIG. 5, the through hole 8 now lies crosswise to the longitudinal slot 4 with which it was previously in communication (FIG. 4).

Figure 6:
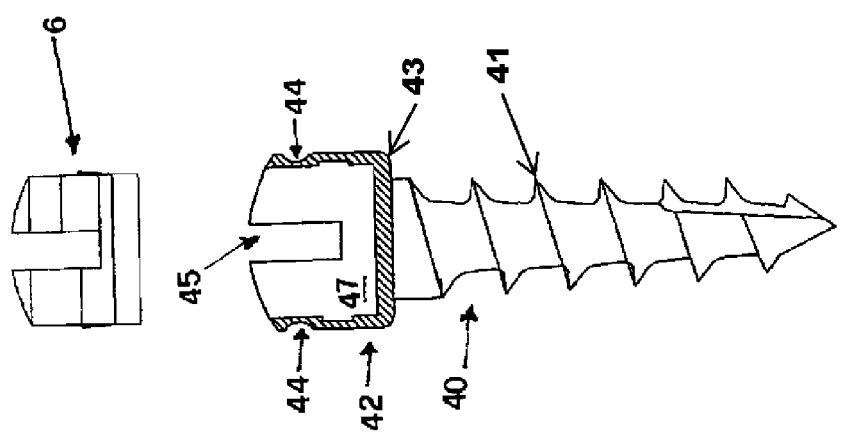
FIG. 6 shows another embodiment of the fixing device according to the invention.
Figure 7:
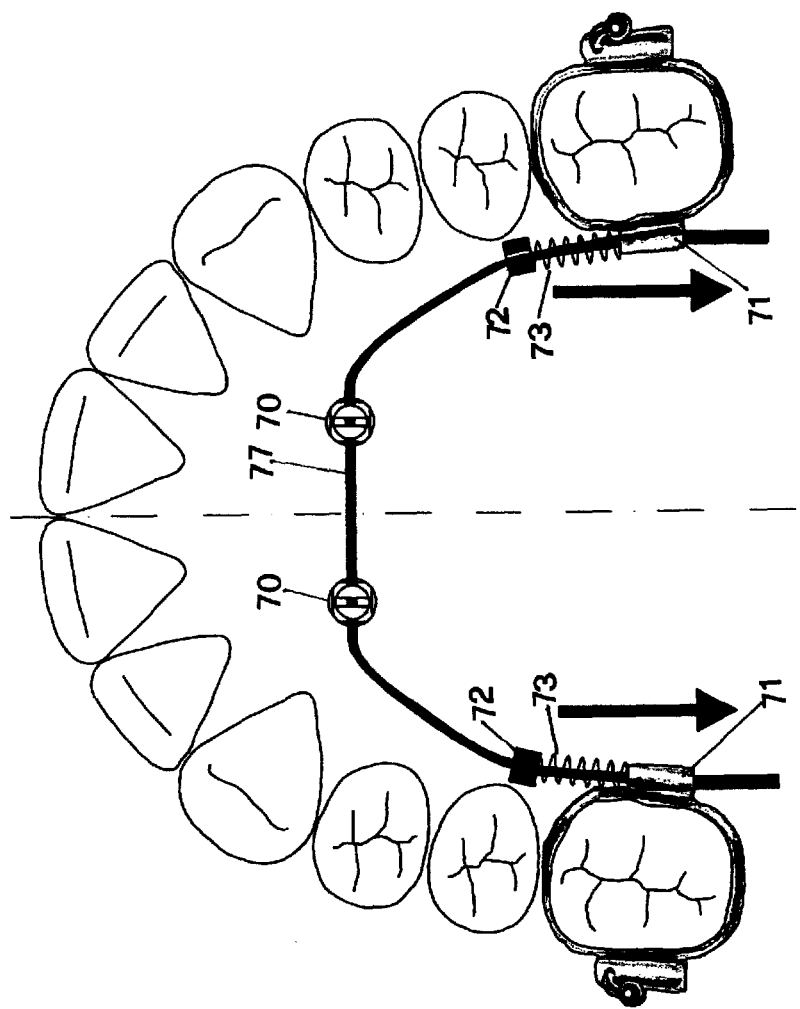

FIG. 6 shows another embodiment of the invention, wherein the screw in the fixing device according to the invention is indicated by the numeral 40.

In the case of this example, said screw 40 has a threaded shaft 41 terminating, on the side of the head 42, with a base 43 that is much smaller in size than the one shown in FIG. 1 and FIG. 2.

In order to provide a seat for housing orthodontic containment wires in the head 42 of the screw 40, there is a ring-shaped cavity 44 on the outer surface of said head. This screw 40 is naturally also complete with a recess 47 inside the head 42 for containing the shaped body 6, and with longitudinal slots 45 for the passage of the orthodontic devices.

In other embodiments of the invention, not shown, more than one ring-shaped cavity may be provided on the outer surface of the head of the screw of the fixing device of the invention.

FIGS. from 7a to 10a show different embodiments of the fixing device according to the present invention.

Figure 7A:
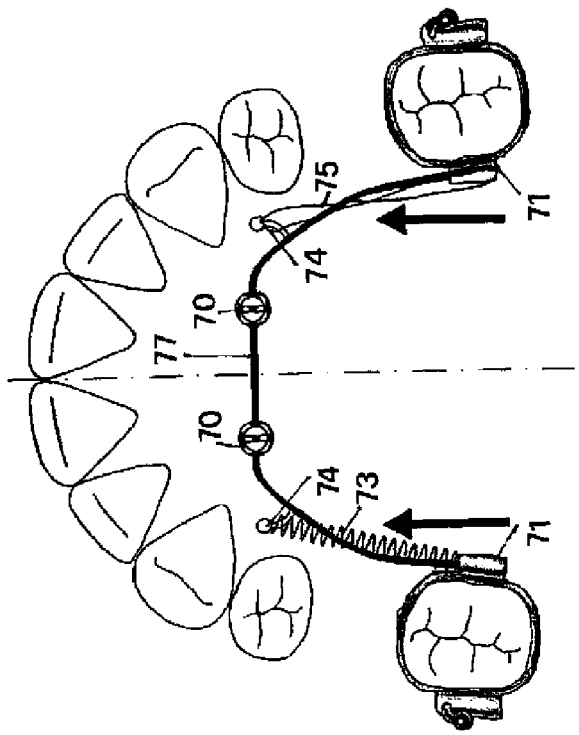
FIGS. 7a and 7b show an orthodontic system anchored to the palate using fixing devices according to the invention.

FIG. 7a shows an orthodontic system for the displacement of the teeth (e.g. for intruding the teeth or for constricting their crosswise diameters, or both) wherein the fixing devices according to the invention consist of two orthodontic screws that are implanted in the palatal area to which a grid and/or a flask and/or a plate are anchored by means of the fixing device according to the present invention.

Springs or elastic bands and/or wires, connected to brackets, buttons and/or bands applied to the teeth, are anchored to the grid or plate or flask.

FIG. 7a shows an orthodontic system consisting of screws 70 according to the invention anchored to the palate and used to fix a palatal arch or orthodontic wire 77. The orthodontic wire 77 is inserted through the palatal tube on two bands 71 attached to the molars.

There are two hooks 74 fixed to the orthodontic wire or palatal arch that are integrally connected to the wire 77.

Elastic bands 75 or springs 73 are drawn from the hooks to the molars that move slidingly forward guided by the wire 77.

FIG. 7b shows an orthodontic system consisting of screws 70 according to the invention, anchored to the palate and used for fixing a palatal arch or orthodontic wire. The orthodontic wire is inserted in the palatal tube on two bands 71 attached to the molars.

A section of tube 72 attached to the orthodontic wire or palatal arch can be fixed in the required antero-posterior position by welding or crimping the orthodontic wire.

This procedure anchors the section of tube 72 in the required position. A thrust spring 73 is inserted between the section of tube 72, fixed in position as explained above, and the palatal tube on the bands 71 attached to the molars.

The spring serves the purpose of pushing the molars towards the distal region (molar distalization) since the hole in the tubes on the bands is of greater diameter than the palatal arch or orthodontic wire.

Figure 8:
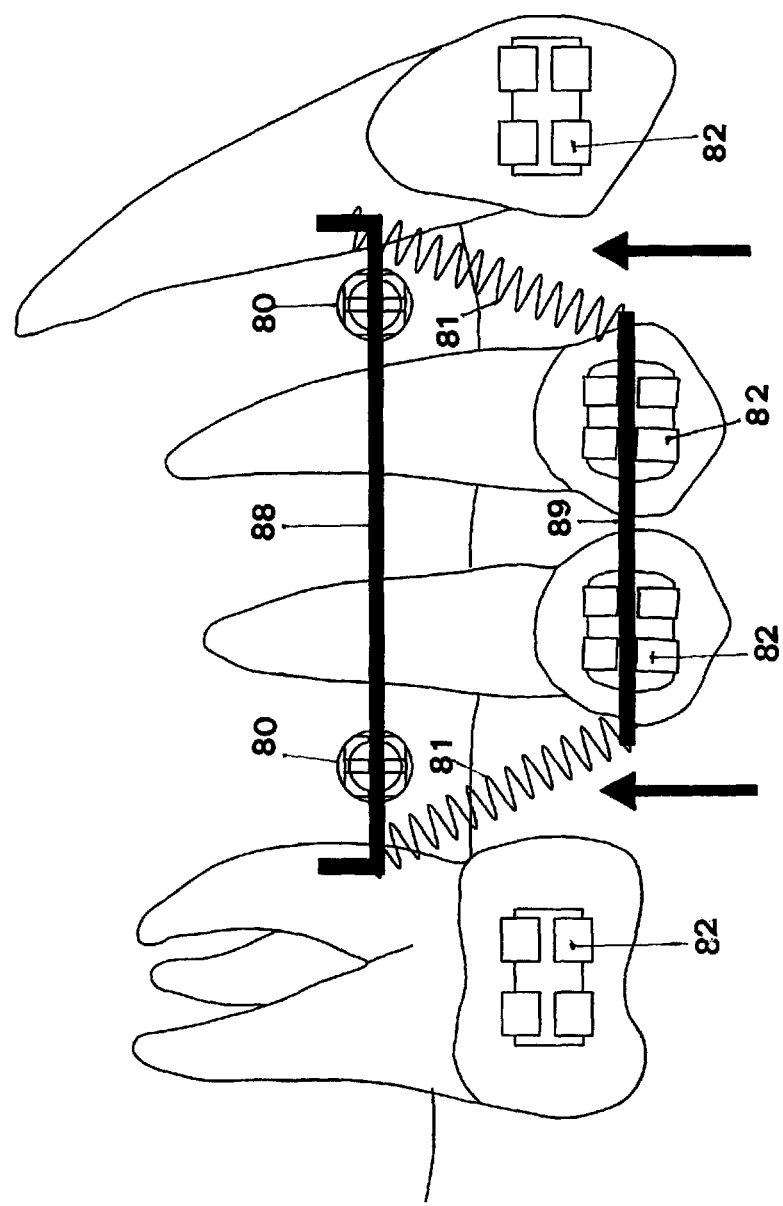
FIG. 8 shows an orthodontic system using fixing devices according to the invention, applied to the vestibular surface of the upper maxilla.

FIG. 8 shows an orthodontic system using the fixing device according to the invention, consisting of two orthodontic screws 80 anchored to the vestibular surface of the upper maxilla.

These two screws inserted in the upper maxilla are used to insert an orthodontic wire 88 that is connected, by means of a plurality of springs 81, to another orthodontic wire 89 anchored by means of a plurality of brackets 82 located on the surfaces of the teeth.

This orthodontic system serves the purpose of intruding several teeth simultaneously.

Figure 9A:
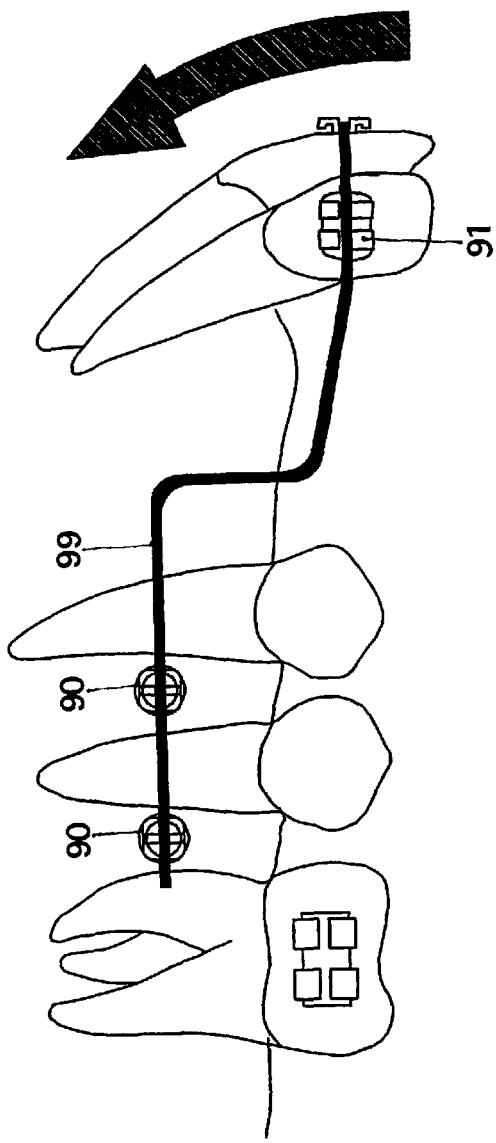

FIG. 9a shows an orthodontic system using the fixing device according to the invention, consisting of two orthodontic screws 90 inserted in the interradicular space.

These screws are used to insert and anchor an orthodontic wire 99, called the intrusion wire (the Ricketts base arch), with elastic characteristics.

The anterior portion of the wire is inserted in the brackets 91 located on the surface of the incisors in order to intrude them, while the rear portion of the wire 99 is inserted in the orthodontic screws forming the object of the invention. By means of suitable deformations, the wire can be activated to intrude the incisors, to extrude them (as shown in FIG. 9b), or to push them forwards (vestibularization) or backwards (retraction).

FIG. 10a shows an orthodontic system using the fixing device according to the invention, consisting of two orthodontic screws 100 inserted in the alveolar bone. These screws are used to insert and anchor an orthodontic wire 101, also shown in FIG. 10b.

Thanks to the characteristics of the fixing device forming part of the orthodontic screws according to the invention, the orthodontic wire 101 can be anchored and consequently prevented from sliding antero-posteriorly or postero-anteriorly.

The suitably modeled wire is composed of a horizontal straight portion 101a, a vertical arm 101b, a ring or circular loop 101c, and a horizontal end 101d with a U-shaped bend 101e serving as an abutment. The horizontal portion 101a is inserted in the screws.

The distal portion 101d is inserted in brackets 102 or a tube attached to the vestibular surface of the molar.

Said orthodontic system serves the purpose of straightening the tooth to which the bracket 102 or tube containing the terminal portion 101d is attached and, with the aid of the ring 101c in the wire, of controlling its vertical position by is adjusting the length of the vertical arm 101b; at the same time, it serves the purpose of distalizing or medializing the tooth as a whole by displacing the horizontal portion 101a of the wire inside the orthodontic screws fitted with the fixing device forwards or backwards.

In fact, when the horizontal portion of the wire 101a inserted in the fixing device forming the object of the invention is displaced backwards, the abutment 101e induces a deformation of the vertical component of the wire 101b that thus serves as a spring and simultaneously has the effect of pushing the tooth backwards (distalization).

Conversely, if the horizontal portion 101a of the wire inserted in the fixing device forming the object of the invention is displaced forwards, and the end portion of the wire 101d is closed with a downward or upward fold immediately beyond the bracket 102 or tube on the tooth, this induces a deformation of the vertical portion 101b of the wire in the opposite direction, which will bring a force of forward displacement (medialization) to bear on the tooth.

Of course, the fixing device according to the invention can also be applied to other applications not shown in the figures.

From the above description, it is clear that the fixing device according to the present invention achieves all the previously stated objects.

In particular, the fixing device according to the invention is removable and enables the orthodontic device to be removed without having to remove the orthodontic screw to which it has been attached.

The fixing device according to the present invention may undergo various modifications that, should they come within the scope of the claims that follow, shall be deemed to be protected by the present patent.

The invention claimed is:

1. An orthodontic fixing device, comprising:
    a screw, said screw including an operating head with a longitudinal slot for receiving at least one orthodontic device, said screw also including a threaded shaft suitable for screwing into an oral cavity, said operating head including a recess; and
    a shaped body, coupled inside a said recess and rotatable in said recess, said shaped body including a through hole for the insertion of one of said at least one orthodontic device, said shaped body also including a shaped slot for retaining said one of said at least one orthodontic device inside said operating head when said shaped body is rotated inside said recess after inserting said one of said at least one orthodontic device in said through hole and in said longitudinal slot, said shaped slot including two opposing surfaces;
    wherein said shaped slot is located inside said shaped body and is in communication with said at least one through hole, said shaped slot lying on a plane substantially orthogonal to the longitudinal axis of said screw; and
    wherein one of said two opposing surfaces is inclined relative to the other surface of the two opposing surfaces, defining between said two opposing surfaces a profile for said shaped slot that converges towards a bottom of said slot, said bottom being defined between said two opposing surfaces, said two opposing surfaces being capable of retaining said one of said at least one orthodontic device inside said operating head by each contacting said at least one orthodontic device when said shaped body is rotated inside said recess.

2. The fixing device according to claim 1, wherein a lateral surface of said shaped body has one or more projections designed to engage inside corresponding ring-shaped cavities prepared located on an inner surface of said recess for containing said shaped body.

3. The fixing device according to claim 2, wherein said one or more projections consist of a single ring-shaped projection.

4. The fixing device according to claim 1, wherein said operating head includes a base for attaching the head to the shaft of said screw.

5. The fixing device according to claim 4, wherein, said fixing device includes a narrowed section in said base of the head.

6. The fixing device according to claim 5, wherein said fixing device includes at least one through hole disposed in said narrowed section.

7. The fixing device according to claim 1, wherein said at least one orthodontic device is an orthodontic wire.

8. The fixing device according to claim 1, wherein said at least one orthodontic device is a part of one of the group consisting of a grid, a flask, and a plate.

9. The fixing device according to claim 3, wherein said fixing device has at least one ring-shaped cavity disposed on an external surface of said head of said screw for containing orthodontic wires.

10. The fixing device according to claim 1, wherein said two opposing surfaces are positioned to clamp said at least one orthodontic device.

11. A multi-component orthodontic fixing device comprising:
    a screw having an operating head and having a threaded shaft that extends longitudinally;
    the operating head including a recess;
    a shaped body rotatably mountable the recess, the shaped body including first and second slots;
    the first slot extending across and through the operating head, and downward into the shaped body toward the threaded shaft;
    the second slot being generally transverse to and intersecting the first slot, the second slot including first and second opposed surfaces;
    wherein the first and second opposed surfaces are spaced apart but inclined toward each other;
    wherein the shaped body is rotatable between first and second positions within the recess of the operating head such that at least one orthodontic device can be inserted into the first slot when the shaped body is in the first position;

wherein the first and second opposed surfaces each is configured to engage the at least one orthodontic device in the second slot when the shaped body is rotated to said second position.

* * * * *